US006203817B1

(12) United States Patent
Cormier et al.

(10) Patent No.: US 6,203,817 B1
(45) Date of Patent: Mar. 20, 2001

(54) REDUCTION OF SKIN REACTIONS CAUSED BY TRANSDERMAL DRUG DELIVERY

(75) Inventors: Michel J. N. Cormier, Mountain View; Peter E. Daddona, Menlo Park; Juanita A. Johnson, Belmont, all of CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/092,606

(22) Filed: Jun. 5, 1998

Related U.S. Application Data

(63) Continuation-in-part of application No. 08/892,118, filed on Jul. 14, 1997.
(60) Provisional application No. 60/038,425, filed on Feb. 19, 1997.

(51) Int. Cl.[7] .................................................... A61F 13/02
(52) U.S. Cl. ...................... 424/464; 424/435; 424/445; 424/447; 424/449; 424/465; 424/466; 424/468; 424/469
(58) Field of Search ..................... 424/435, 445, 424/447, 449, 464, 465, 466, 468, 469

(56) References Cited

U.S. PATENT DOCUMENTS

| 429,356 | 5/1890 | Holland ............................... 424/274 |
|---|---|---|
| 3,598,122 | 8/1971 | Zaffaroni ............................. 128/268 |
| 3,598,123 | 8/1971 | Zaffaroni ............................. 128/268 |
| 3,731,683 | 5/1973 | Zaffaroni ............................. 128/268 |
| 3,797,494 | 3/1974 | Zaffaroni ............................. 128/268 |
| 4,031,894 | 6/1977 | Urquhart et al. .................... 128/268 |
| 4,035,511 | 7/1977 | Messing et al. ..................... 424/330 |
| 4,083,982 | 4/1978 | Messing et al. ..................... 424/260 |
| 4,144,317 | 3/1979 | Higuchi et al. ....................... 424/21 |
| 4,201,211 | 5/1980 | Chandrasekaran .................. 128/268 |
| 4,286,592 | 9/1981 | Chandrasekaran .................. 128/260 |

(List continued on next page.)

FOREIGN PATENT DOCUMENTS

| 43 01 783 C1 | 2/1994 | (DE) | ............................... A61L/15/44 |
|---|---|---|---|
| 92/18005 | 10/1992 | (WO) | ............................ A01N/43/62 |
| 92/19226 | 11/1992 | (WO) | ............................... A61K/9/16 |
| 94/21262 | 9/1994 | (WO) | ............................. A61K/31/55 |
| 95./01167 | 1/1995 | (WO) | ............................... A61K/9/70 |
| 95/09006 | 4/1995 | (WO) | ............................. A61K/47/14 |
| 95/28151 | 10/1995 | (WO) | ............................ A61K/31/135 |
| 96/37231 | 11/1996 | (WO) | ............................. A61K/47/14 |
| 96/40259 | 12/1996 | (WO) | ............................. A61K/47/14 |
| 97/10816 | 3/1997 | (WO) | ............................. A61K/31/13 |

OTHER PUBLICATIONS

Knepp, Victoria M., et al., Transdermal Drug Delivery: Problems and Poasibilities, CRC Critical Reviews in Therapeutic Drug Carrier Systems, vol. 4, Issue 1 (1987), pp. 13–37.

Cleary, Gary W., Topical Drug Bioavailability: Bioequivalence, and Penetration, (1993), Transdermal Delivery Systems: A Medical Rationale, pp. 17–68.

*Primary Examiner*—S. Mark Clardy
*Assistant Examiner*—Kathryne E. Shelborne
(74) *Attorney, Agent, or Firm*—Owen J. Bates; Steven F. Stone; Vandana Date

(57) ABSTRACT

Transdermal compositions, devices, and methods for the administration of a drug at reduced skin irritation levels are disclosed. More particularly, this invention relates to novel methods, compositions, and devices for the reduction or elimination of irritation or sensitization caused by an irritating or sensitizing drug when it is delivered transdermally. According to a preferred embodiment, transdermal administration of a drug salt of a non-zwitterionic drug is disclosed wherein the drug salt comprises a combination of surface activity and a low octanol-water partition coefficient. Such drug salts have been found to reduce irritation or sensitization to the drug being delivered while achieving therapeutically effective transdermal fluxes.

27 Claims, 10 Drawing Sheets

U.S. PATENT DOCUMENTS

| | | | |
|---|---|---|---|
| 4,314,081 | 2/1982 | Molloy et al. | 564/347 |
| 4,314,557 | 2/1982 | Chandrasekaran | 128/260 |
| 4,329,356 | 5/1982 | Holland | 424/274 |
| 4,379,454 | 4/1983 | Campbell et al. | 604/897 |
| 4,435,180 | 3/1984 | Leeper | 604/896 |
| 4,444,778 | 4/1984 | Coughlin | 424/262 |
| 4,552,872 | 11/1985 | Cooper et al. | 514/175 |
| 4,559,222 | 12/1985 | Enscore et al. | 424/28 |
| 4,568,343 | 2/1986 | Leeper et al. | 604/896 |
| 4,573,995 | 3/1986 | Chen et al. | 604/896 |
| 4,588,580 | 5/1986 | Gale et al. | 424/21 |
| 4,590,213 | 5/1986 | Stark | 514/653 |
| 4,594,358 | 6/1986 | Hynes | 514/651 |
| 4,626,549 | 12/1986 | Molloy et al. | 514/651 |
| 4,645,502 | 2/1987 | Gale et al. | 604/896 |
| 4,647,591 | 3/1987 | Cherkin et al. | 514/651 |
| 4,683,235 | 7/1987 | Hynes | 514/282 |
| 4,704,282 | 11/1987 | Campbell et al. | 424/449 |
| 4,746,515 | 5/1988 | Cheng et al. | 424/449 |
| 4,756,710 | 7/1988 | Bondi et al. | 424/449 |
| 4,788,062 | 11/1988 | Gale et al. | 424/449 |
| 4,816,258 | 3/1989 | Nedberge et al. | 424/448 |
| 4,849,226 | 7/1989 | Gale | 424/448 |
| 4,863,738 | 9/1989 | Taskovich | 424/449 |
| 4,865,848 | 9/1989 | Cheng et al. | 424/449 |
| 4,888,354 | 12/1989 | Chang et al. | 514/424 |
| 4,895,845 | 1/1990 | Seed | 514/252 |
| 4,904,475 | 2/1990 | Gale et al. | 424/449 |
| 4,908,027 | 3/1990 | Enscore et al. | 604/890 |
| 4,938,759 | 7/1990 | Enscore et al. | 604/896.1 |
| 4,940,585 | 7/1990 | Hapworth et al. | 424/464 |
| 4,943,435 | 7/1990 | Baker et al. | 424/448 |
| 4,999,382 | 3/1991 | Wurtman et al. | 514/646 |
| 5,000,956 | 3/1991 | Amkraut et al. | 424/434 |
| 5,004,610 | 4/1991 | Osborne et al. | 424/448 |
| 5,028,431 | 7/1991 | Franz et al. | 424/449 |
| 5,049,387 * | 9/1991 | Amkraut | 424/435 |
| 5,104,899 | 4/1992 | Young et al. | 514/646 |
| 5,122,382 | 6/1992 | Gale et al. | 424/449 |
| 5,141,750 | 8/1992 | Lee et al. | 424/448 |
| 5,151,448 | 9/1992 | Crenshaw et al. | 514/651 |
| 5,225,585 | 7/1993 | Schwartz et al. | 558/275 |
| 5,314,694 | 5/1994 | Gale et al. | 424/448 |
| 5,342,623 | 8/1994 | Enscore et al. | 424/448 |
| 5,356,934 * | 10/1994 | Robertson et al. | 514/649 |
| 5,378,730 | 1/1995 | Lee et al. | 514/535 |
| 5,411,738 | 5/1995 | Hind | 424/445 |
| 5,446,070 | 8/1995 | Mantelle | 514/772.6 |
| 5,451,707 | 9/1995 | Cormier et al. | 424/448 |
| 5,589,511 | 12/1996 | Young et al. | 514/646 |
| 5,589,512 | 12/1996 | Norden | 514/646 |
| 5,601,839 | 2/1997 | Quan et al. | 424/448 |
| 5,635,203 | 6/1997 | Gale et al. | 424/448 |
| 5,641,504 | 6/1997 | Lee et al. | 424/447 |
| 5,785,991 * | 7/1998 | Burkoth et al. | 424/448 |

* cited by examiner

Fluoxetine Urinary Excretion in the Hairless Guinea Pig *

* 2 cm² system, n = 3, 24 h wearing (except iv), excretion expressed as fluoxetine base

Irritation and Flux of Fluoxetine Salts in the Hairless Guinea Pig *

* 2 cm² system, n = 3, 24 h wearing

Irritation and Log P of Fluoxetine Salts in the Hairless Guinea Pig *

* 2 cm² system, n = 3, 24 h wearing

Effect of pH on Fluoxetine-induced Skin Irritation in the Hairless Guinea Pig *

* Fluoxetine acetate 0.66 M, 2 cm$^2$ system, n = 3, 24 h wearing

REDUCTION OF SKIN REACTIONS CAUSED BY TRANSDERMAL DRUG DELIVERY

RELATED APPLICATIONS

This application is a continuation-in-part of Ser. No. 08/892,118, filed Jul. 14, 1997, and Provisional application Ser. No. 60/038,425, filed Feb. 19, 1997, for which benefit is claimed of its earlier filing date.

FIELD OF INVENTION

This invention relates to the passive transdermal delivery of drugs at acceptable skin irritation levels. More particularly, this invention relates to novel methods, compositions, and devices for the reduction or elimination of irritation and/or sensitization caused by an irritating or sensitizing drug when it is delivered transdermally. Still more particularly, but without limitation thereto, this invention relates to the passive transdermal delivery of drug salts possessing a combination of surface activity and low octanol-water partition coefficients whereby the drug salts may be transdermally administered at therapeutically effective drug fluxes and acceptable irritation and/or sensitization levels to the drug being delivered.

BACKGROUND OF THE INVENTION

The transdermal route of parenteral drug delivery provides many advantages over other administrative routes. Transdermal systems for delivering a wide variety of drugs or other beneficial agents are described in U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,568,343; 4,573,995; 4,588,580; 4,645,502; 4,698,062; 4,704,282; 4,725,272; 4,781,924; 4,788,062; 4,816,258; 4,849,226; 4,904,475; 4,908,027; 4,917,895; 4,938,759; 4,943,435; 5,004,610; 5,071,656; 5,122,382; 5,141,750; 5,284,660; 5,314,694; 5,342,623; 5,411,740; and 5,635,203, which are hereby incorporated in their entirety by reference.

The factors influencing transdermal permeability of the stratum corneum can be classified into three major categories: 1) physicochemical properties of the penetrant; 2) physicochemical properties of the drug delivery system; and 3) physiological and pathological conditions of the skin. Various models based upon physicochemical data have been proposed to predict the transdermal flux of pharmaceutically active agents. Such models correlate the permeability of the skin to a specific penetrant ($K_p$) with the diffusion coefficient of the penetrant through the skin ($D_s$) and partition coefficient (k) between the lipophilic stratum corneum and more aqueous in nature viable tissue. These models are based upon Fick's Law of Diffusion and may be represented by the following simplification:

$$K_p = (D_s)(k_m)/l \qquad (1)$$

where $k_m$ represents the partition coefficient of the penetrant between membrane m and the contacting solution and l represents the diffusion path length.

Because the measurement of $k_m$ is difficult, the more readily available octanol-water partition coefficient, $k_{oct}$, is often used and is often expressed as the logarithm, log P. In general, drugs with high log P values are more likely to permeate through skin. Based upon such models, it has been concluded that drugs of high water solubility and a strong tendency to partition into oils can be expected to be quite skin permeable. It has also been concluded that one would expect the specific permeability of skin to the non-ionized form of a drug to be substantially greater that that of the ionized form. However, if the water solubility of the free base, non-ionized form of the drug is much less than that of its ionized salt, its rate of permeation in non-ionized form may be lower than that of its salt, even though the intrinsic permeability of the skin for the free base may be much greater. See Y. W. Chien, *Transdermal Controlled-Release Drug Administration,* Novel Drug Delivery systems—Fundamentals, Development Concepts, Biomedical Assessments, Marcel Dekker Inc., N.Y. 1982; and Guy et al., *Physicochemical Aspects of Percutaneous Penetration and Its Enhancement,* Pharmaceutical Research, Vol. 5, No. 12, 1988, which are hereby incorporated in their entirety by reference.

More recent models have refined the correlation between the partition coefficient $k_m$ in equation (1) with the octanol-water partition coefficient $k_{oct}$ (log P). Potts et al. express the relationship as:

$$k = [k_{oct}]^f \qquad (2)$$

where the coefficient f accounts for the difference between the partitioning domain presented by octanol and that presented by the stratum corneum lipids.

Additionally, the functional dependence of $D_s$ on molar volume has been taken into account in contrast to the assumption in Equation (1) that it remain constant for all permeants. For many compounds, the molecular weight is a reasonable approximation for molar volume, thus the molar volume term may be approximated by using the molecular weight. As a result, these parameters have been used to develop quantitative structure-activity relationships (QSARs) which can be useful in predicting skin permeability coefficients for various chemicals. See Potts et al., *Predicting Skin Permeability,* Pharmaceutical Research, Vol. 9, no. 5, 1992 and Kirchner et al., *The Prediction of Skin Permeability by Using Physicochemical Data,* ATLA 25, 1997, which are hereby incorporated in their entirety by reference.

Unfortunately, many drugs that are candidates for transdermal delivery based upon such models have a tendency to cause skin irritation to human patients, particularly when maintained in contact with the skin under occlusion for sustained periods of time. These irritating drugs can cause undesirable skin reactions, such as itching and erythema. Therefore, despite the development of the transdermal drug delivery art, there remains a continuing need for an improved method of overcoming irritation caused by transdermal delivery of an irritating drug while transdermally delivering drugs at therapeutically effective rates.

Skin irritation can be caused by a variety of factors including, but not limited to, physical factors, eg, chafing or occluding the skin in an airtight manner; exposure to certain chemicals; exposure to pH outside normal pH of the skin or mucosa; and bacterial overgrowth. The skin reacts to many topically applied substances, particularly those maintained under occlusion, by blistering or reddening accompanied by unpleasant burning, itching, and stinging sensations. There is a wide interpersonal variation and susceptibility to irritation. An agent must be minimally irritating in a large percentage of the potential patient population in order to be suitable for safe and effective transdermal administration. Generally, tissue irritation is the manifested result of damage or toxicity to cells in the skin or mucosa caused by their response to a cytotoxic, i.e., irritating, agent.

There are known methods available to decrease the incidence of drug and permeation enhancer induced irritation and sensitization. Such methods include the codelivery of methyl nicotinate as disclosed in U.S. Pat. No. 5,451,407; codelivery of an anti-inflammatory agent as disclosed in U.S. Pat. Nos. 5,171,576 and 5,077,054; codelivery of a lysosomal uptake inhibitor as disclosed in U.S. Pat. Nos. 5,130,139 and 5,160,741; codelivery of a metabolic modulator as disclosed in U.S. Pat. No. 5,304,379; codelivery of an antigen processing-inhibiting agent as disclosed in U.S. Pat. Nos. 5,120,545 and 5,149,539; codelivery of glycerine as disclosed in U.S. Pat. No. 4,855,294; controlling the pH in the drug reservoir in order to deliver the non-ionized form of the drug at reduced irritation as disclosed in U.S. Pat. No. 4,756,710 and delivery of a non-irritating pro-drug. All of the above patents are hereby incorporated in their entirety by reference.

If a method involves codelivery of an agent and drug, precise codelivery of both the agent and drug is necessary. Not only might the precise codelivery of the drug and agent be difficult to achieve, but also codelivery of the irritation inhibitor may cause regulatory concerns. With respect to the delivery of a nonirritating pro-drug, although this method may potentially be efficient, the method for delivery is cumbersome and a new chemical entity is being delivered, thus causing regulatory concerns.

Reduction of irritation likely also results in a decrease in the sensitization reaction. Sensitization is an allergic reaction which is induced when an agent is first applied to the skin and is elicited upon continued exposure which may occur immediately or after a long period of seemingly harmless exposure. Sensitization may be local, elicited by topical exposure that manifests itself as contact dermatitis accompanied by blistering, itching, reddening, and burning at the site of application. More seriously, the sensitization may be systemic, elicited by topical application that manifests itself by more general allergic reactions at sites other than the site of application. Most seriously, the systemic sensitization may be elicited by oral or intravenous administration of the drug. If the latter occurs, the patient will be unable to take the drug by any route of administration.

It is well known that irritation increases the sensitization potential of sensitizers. In fact, testing in animals is indeed often accomplished in the presence of a skin irritant such as sodium dodecyl sulfate (SDS) in order to increase the sensitization potential of the compound being evaluated.

While the passive transdermal administration of various salt forms of drugs is disclosed in the prior art, it has typically been at the cost of reduced flux of the salt form compared to that of the base form of the drug as predicted by the various models above. To overcome the low fluxes associated with transdermal administration of drug salts, a permeation enhancer such as isopropanol is provided as disclosed in U.S. Pat. No. 5,374,645.

Additionally, U.S. Pat. No. 4,888,354 discloses the transdermal administration of active pharmaceutical permeants present as a combination of both free base and acid addition salt forms. It is disclosed that the combination provides enhanced skin penetration rates compared to either the free base or acid addition salt utilized separately. The active agent is formulated in a carrier which preferably possesses skin permeation enhancement activity.

U.S. Pat. No. 4,740,374 discloses anti-inflammatory analgesic adhesive preparations comprising a salt form of the anti-inflammatory analgesic uniformly dissolved in a pressure sensitive adhesive.

U.S. Pat. No. 5,073,539 discloses compositions of zwitterionic drugs for transdermal administration and methods for administering zwitterionic drugs transdermally. The compositions comprise a zwitterionic drug in a salt form and a solvent therefor.

U.S. Pat. No. 5,422,118 discloses the transdermal administration of skin irritating amines in a manner that minimizes skin irritation by providing the amine as a salt of a stoichiometric molar excess of a fatty acid of from 8 to 20 or 22 carbon atoms in a non-polar, nonvolatile solvent.

U.S. Pat. No. 5,438,067 discloses transdermal delivery systems for administering medetomidine. Medetomidine salts having a log P value in the range 1.2 to 3.4 (in octanol/water) were found to result in equal or better flux than medetomidine free base.

U.S. Pat. No. 5,462,744 relates to transdermal systems that maintain a constant pH level on the skin, comprising an additive which buffers the pH on the skin's surface U.S. Pat. No. 5,614,178 discloses pharmaceutical compositions for topical application for enhancing the skin penetration of drugs with reduced skin irritation comprising cationic polymers, nonionic surfactants and water-immiscible solubilizing aids. All of the above mentioned patents are hereby incorporated in their entirety by reference.

Despite the above, there remains a need to reduce or eliminate the irritation potential of a transdermally administered drug while improving the transdermal flux.

By reducing the drug-induced irritation it is likely that the sensitization reaction is also reduced. While the above patents and articles provide models for predicting skin permeability to a particular penetrant based upon the penetrant's log P value, the inventors are not aware of any models or teachings that attempt to identify drug salts suitable for transdermal administration at therapeutically effective rates at acceptable irritation and/or sensitization levels based on log P values and surface activity.

Description of Terms

As used herein, the term "acceptable irritation level" refers to a Primary Irritation Index (PII) of less than 5.0 (moderate), preferably less than 2.0 (mild), as measured by the method of Draize et al. (See Draize et al. "Methods for the study of irritation and toxicity of substances applied topically to the skin and mucous membranes" J. Pharmacol Exp Therap 1944; 82: 377–390, hereby incorporated in its entirety by reference).

As used herein, the term "drug" refers to a biologically active agent, compound or composition of matter that is administered for the purpose of providing some beneficial or therapeutic affect.

As used herein, the term "lag time" refers to the delay between the time when a transdermal device is first applied and when therapeutically effective blood levels are first achieved.

As used herein, the term "permeation enhancer" intends an agent or a mixture of agents which acts to increase the permeability of the skin to drug.

As used herein, the term "permeation-enhancing amount" intends an amount of a permeation enhancer which provides permeation enhancement throughout a substantial portion of the administration period.

As used herein, the phrase "predetermined area of skin" intends a defined area of intact unbroken skin or mucosal tissue. That area will usually be in the range of about 5 $cm^2$ to about 100 $cm^2$.

As used herein, the term "predetermined delivery period" refers to the delivery of drug for a time period of from several hours to seven days or longer. Preferably, the time period is from 12 hours to 3 or 4 days.

As used herein, the term "surface activity" refers to drug salts capable of reducing the surface tension of water at concentrations lower than 0.1 M to at least 50 Dynes/cm.

As used herein, the phrase "sustained time period" or "administration period" intends at least about 8 hours and will typically intend a period in the range of about one to about seven days.

As used herein, the term "therapeutically effective" amount or rate refers to the amount or rate of drug or active agent needed to affect the desired therapeutic result.

As used herein, the term "transdermal" delivery or administration refers to the delivery of agents by passage through skin, mucosa, and/or other body surfaces by topical application.

SUMMARY OF THE INVENTION

The present invention overcomes the problems in the prior art by providing compositions, devices, and methods for transdermally administering drugs at therapeutically effective rates at acceptable irritation and sensitization levels. According to the invention, improved compositions, devices, and methods for transdermal administration of non-zwitterionic drugs are disclosed wherein the compositions and devices are provided with a salt of a non-zwitterionic drug which possesses a combination of surface activity and a low log P value. In another aspect, the present invention provides a method to select a preferred drug salt from among the pharmaceutically acceptable salts of the drug.

Accordingly, it is an aspect of this invention to provide compositions, devices, and methods for the transdermal administration of a drug at acceptable irritation levels.

It is another aspect of this invention to provide improved compositions, devices, and methods for the transdermal administration of a non-zwitterionic drug by administering a salt form of the drug which possesses surface activity.

It is another aspect of this invention to reduce the skin depot of drug accumulating in the skin during transdermal administration.

It is another aspect of this invention to reduce the lag time associated with transdermal drug delivery.

Additional aspects and advantages of the invention will be set forth in part in the description which follows, and in part will be obvious from the description, or may be learned by the practice of the invention. The aspects and advantages of the invention will be obtained by means of the instrumentalities and combinations particularly pointed out in the appended claims.

The system of the invention comprises a carrier or matrix adapted to contain a salt form of a non-zwitterionic drug wherein the drug salt possesses surface activity and a low log P value. The matrix or carrier is placed in a drug-transmitting relation with the selected skin or mucosa site. The matrix or carrier contains sufficient amounts of the drug salt to continuously administer it to the skin or mucosa site at a therapeutically effective rate over a predetermined delivery period at acceptable irritation levels. A device for carrying out the invention may be a passive transdermal device known in the art such as those described in the aforementioned patents.

The accompanying Figures which are incorporated in and constitute a part of the specification, illustrate embodiments of the invention and, together with the description, serve to explain the principals of the invention.

DETAILED DESCRIPTION OF THE INVENTION

Figure 1:
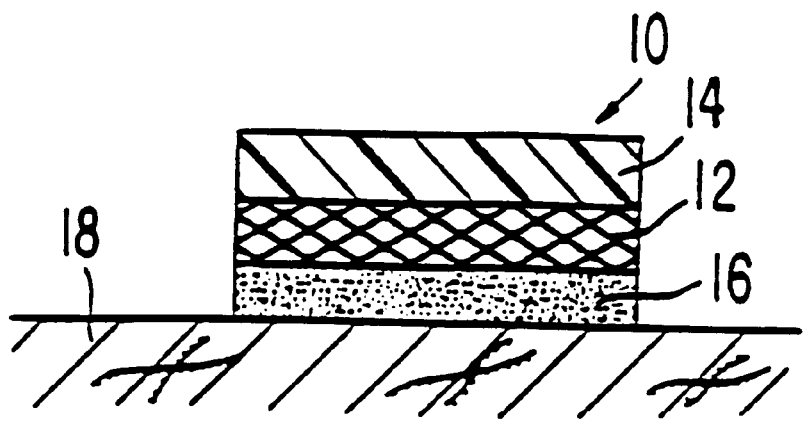
FIG. 1 is a cross-sectional view of one embodiment of a transdermal therapeutic drug delivery device that may be used in accordance with the present invention.

The present inventors have found that drug salts possessing a combination of surface activity and a low log P value may be administered transdermally at therapeutically effective rates at acceptable irritation levels. Surprisingly, it has been discovered that non-zwitterionic drug salts having low log P values can be transdermally administered at therapeutically effective rates. This is contrary to the various models discussed above which suggest that suitable candidates for transdermal drug delivery require high log P values.

The drug salts according to this invention comprise the drug and a counterion wherein the counterion possesses substantially no intrinsic surface activity. Drug salts according to this invention penetrate the skin at therapeutically effective rates without requiring additional permeation enhancers, though permeation enhancers known in the art may be utilized to increase flux. It is believed that the drug salts according to this invention have surfactant-like activity and act as their own permeation enhancers. Additionally, transdermal administration of drug salts according to this invention has unexpectedly been found to reduce the skin depot of drug accumulating in the skin and the associated lag time.

Transdermal administration of drug salts according to this invention results in reduced skin irritation at equivalent flux of the non-ionized irritating form of the drug. While not being limited to any particular theory, it is believed that transdermal administration of the non-ionized form of the drug causes pH changes within the skin which results in unacceptable irritation. The inventors have found that the extracellular pH has an effect on the cytotoxicity of a drug and that skin irritation levels increase with the drug cytotoxicity. Transdermal administration of acidic or basic drugs in their acidic or basic form causes the pH within the skin to decrease or increase, respectively, which in turn causes increases in drug uptake by cells, and increases in cytotoxicity and, therefore, skin irritation.

On the other hand, transdermal administration of the drug as a salt does not result in pH changes within the skin and therefore does not cause the skin irritation associated with the transdermal administration of the acidic or basic form. In addition, excess of free acid in the case of a basic drug or excess of free base in the case of an acidic drug will cause the pH within the skin to decrease or increase, respectively, which in turn further reduces drug uptake by cells and results in an additional reduction in cytotoxicity and, therefore, further reduction in irritation.

The drug salts according to this invention are selected such that they penetrate the skin at therapeutically effective rates. A preferred embodiment is directed to drug salts demonstrating a critical micelle concentration (CMC). According to this embodiment, the salt form is selected by measuring its CMC in water by methods known in the art, for example, by the use of a surface tensiometer.

For example, CMC values for chlorpromazine acetate and fluoxetine acetate in water were found to be $2\times10^{-2}$ M and $5\times10^{-2}$ M, respectively. The CMC provides a measure of the surface activity of the particular drug salt. A preferred embodiment is directed to the transdermal administration of drug salts having a CMC of less than about 0.5 M, more preferably between $10^{-6}$–$10^{-1}$ M, and a log P value of less than 1.0, preferably less than 0.8, in the drug concentration range of $10^{-3}$–$10^{-1}$ M.

According to a preferred embodiment, the drug to be administered is capable of micellar aggregation. Examples of drugs comprising surface activity and capable of micellar aggregation according to this invention include, but are not limited to, diphenylmethane derivatives with antihistaminic activity such as cyclizine, chlorcyclizine, bromodiphenhydramine, diphenylpyraline, diphenhydramine, chlorcyclizine, medrilamine, phenyltoloxamine clemastine and all other diphenylmethane derivatives presenting antihistaminic properties that are capable of micellar aggregation; pyridine derivatives with antihistaminic activity such as chlorpheniramine, brompheniramine, pheniramine, mepyramine, tripelennamine, chloropyramine, thenyidiamine, methapyrilene and all other pyridine derivatives presenting antihistaminic properties that are capable of micellar aggregation; diphenylmethane derivatives with anticholinergic activity such as adiphenine, piperidolate, benztropine, orphenadrine, chlorphenoxamine, lachesine, poldine, pipenzolate, clidinium, benzilonium, ambutonium; anticholinergic agents such as oxybutynin, oxyphenonium, tricyclamol, dicyclomine, glycopyrronium, penthienate; antidepressant drugs such as fluoxetine, iprindole, imipramine, clomipramine, desipramine, trimipramine, amitriptylline, nortriptylline, noxiptiline, butriptiline, doxepin, dothiepin, iprindole, protryptiline, melitracene, dimetacrine, opipramol, paroxetine, sertraline, citalopram; tranquillizers such as promazine, chlorpromazine, chlorproethazine, methoxypromazine, methpromazine, promethazine, dimethothiazine, methiomeprazine, trimeprazine, methiotrimeprazine, diethazine, thioridazine, perazine, trifluoperazine, thioperazine, thiethylperazine, perphenazine, fluphenarine thiopropazate, thiothixene, chlorprothixene; antipsychotics such as pimozide, thiopropazate, flupenthixol, clopenthixol, trifluoperazine, olanzapine; anorexics such as fenfluramine and chlorphentermine; analgesics such as methadone and dextropropoxyphene; non steroidal antiinflammatory compounds such as diclofenac and indometacin; local anaesthetics such as tetracaine, stadacaine, cinchocaine, lidocaine; antihypertensives such as propranolol, oxprenolol, acebutolol, sotalol, metoprolol; prostaglandins; antiarrhythmic and antianginals such as amiodarone, dilthiazem and verapamil; antiestrogen such as tamoxifen; and antiosteoporotic agents such as raloxifen.

According to a preferred embodiment, the drug to be administered possesses at least one pKa between about 6.0–12.0 for basic drugs or at least one pKa between about 2.0–8.0 for acidic drugs, and is capable of micellar aggregation.

Most preferably, the drug is selected from small amphiphillic drugs having a molecular weight of less than 1000. Preferred drugs according to this embodiment include, but are not limited to, citalopram, fluoxetine, fentanyl, olanzapine, oxybutynin, raloxifene, paroxetine, and chlorpromazine. Fluoxetine acetate is a particularly preferred drug salt according to this invention.

According to a preferred embodiment, the drug salt is a pharmaceutically acceptable organic or inorganic salt such as an acid addition salt of a monocarboxylic or polycarboxylic acid and includes, but is not limited to, acetate, propionate, butyrate, pentanoate, hexanoate, heptanoate, chloride, bromide, citrate, succinate, maleate, glycolate, gluconate, glucuronate, 3-hydroxyisobutyrate, 2-hydroxyisobutyrate, lactate, malate, pyruvate, tartarate, tartronate, nitrate, benzene sulfonate, methane sulfonate, sulfate, sulfonate, and fumarate for basic drugs; and sodium, potassium, calcium, magnesium, ammonium, monoethanolamine, diethanolamine, triethanolamine, tromethamine, lysine, methylglucamine, morpholine, histidine, and arginine for example, for acidic drugs.

The drug and counterion are preferably combined in stoichiometric equimolar amounts for monoacidic counterions. With counterions bearing two acidic functions, such as maleate, the drug is combined with only half the equimolar amount of acid while only one third of the equimolar amount of acid is used for counterions bearing three acidic functions, such as citrate. Excess of counterion (either as the non-conjugated or conjugated acid or base) can be added to the drug in order to control pH. Mixtures of different counterions can also be used.

A preferred embodiment is directed to buffered formulations. For basic drugs, an excess of a weak acid including, but not limited to acetic acid, propionic acid, lactic acid, malic acid, or glycolic acid, is added to the formulation in order to control pH. For acidic drugs, an excess of a weak base including, but not limited to, ammonium, monoethanolamine, diethanolamine, triethanolamine, tromethamine, lysine, methylglucamine, morpholine, histidine, and arginine is added to the formulation. According to this preferred embodiment, the weak base or weak acid, preferably acetic acid, is added to adjust the pH of the formulation to a preferred pH range of about 4–7. The pH is preferably adjusted to be at least 3, preferably at least 4 pH units away from the pKa of the drug. The mole ratio of weak acid or base/drug is preferably between 1–7, most preferably between 1.5–5.5.

An advantage in using a drug salt having surface activity comes from the fact that the solubility of additional components of the formulation can be enhanced, such as, for example, anti-irritants as known in the art. For example, hydrocortisone has a very low solubility in water and a rather poor solubility in non aqueous solvents. The solubility of hydrocortisone is greatly enhanced in the presence of fluoxetine acetate in water or in mixed solvents. This increased solubility is expected to result in higher hydrocortisone skin flux and even lower skin irritation levels.

Figure 3:
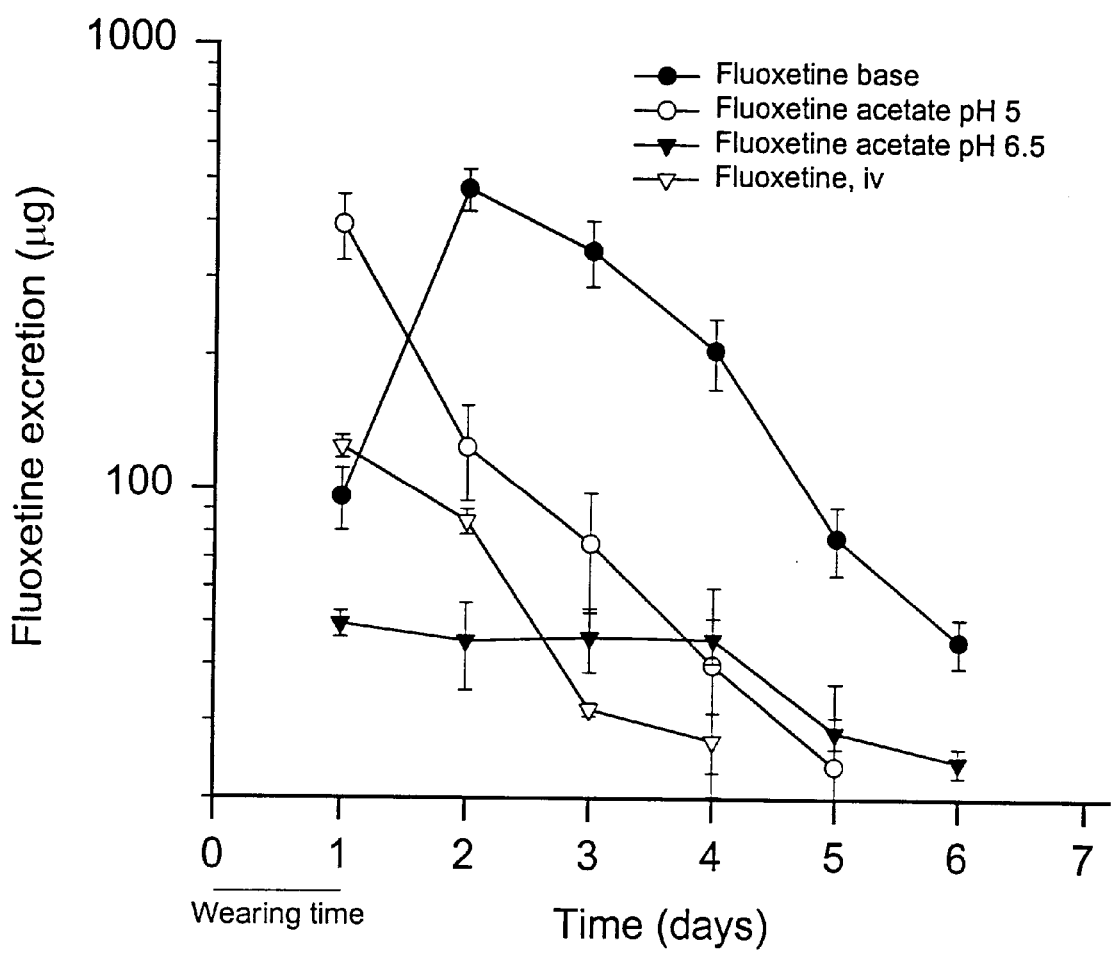
FIG. 3 is a graph depicting fluoxetine urinary excretion as a function of time.

Another advantage in the use of the salt form of a drug is reflected in FIG. 3 which represents the urinary excretion of fluoxetine as a function of time. This graph shows that the kinetics of urinary excretion of fluoxetine is dramatically different according to the form administered transcutaneously. With fluoxetine base, a skin depot is observed. With fluoxetine acetate (pH 6.5), the skin depot is reduced but is still present. With fluoxetine acetate acidified with excess acetic acid to pH 5, the skin depot is eliminated as the kinetics of elimination is close to that observed following intravenous administration of the drug.

According to the present invention, the drug salt is typically dispersed within a physiologically compatible matrix or carrier as more fully described below, which is placed in a drug transmitting relation with the appropriate body surface and maintained in place for the desired period of time. Such placement and ensuing transdermal permeation of the drug salt will result in lower irritation as compared to that produced by the non-ionized species. The composition may be applied directly to the body as an ointment, gel, cream, suppository or sublingual or buccal tablet, for example, or they may be administered from a matrix or carrier in a transdermal therapeutic delivery device.

Figure 2:
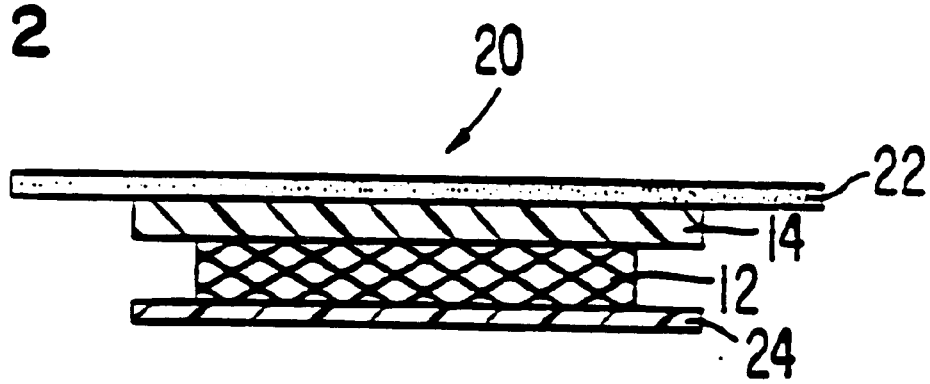
FIG. 2 is a cross-sectional view of another embodiment of a transdermal therapeutic drug delivery device that may be used in accordance with the present invention.

Two examples of suitable transdermal delivery devices are illustrated in FIGS. 1 and 2. In FIG. 1, transdermal device 10, comprises a reservoir 12, containing the drug salt. Reservoir 12 is sandwiched between a backing layer 14 and an adhesive layer 16. Optionally, a rate-controlling membrane or a tie layer membrane as disclosed in U.S. Pat. No. 5,635,203 (not shown) may be present between reservoir 12 and adhesive layer 16. In FIG. 1, the reservoir 12 is formed of a material, such as a rubbery polymer, that is sufficiently viscous to maintain its shape. If a lower viscosity material is used for reservoir 12, such as an aqueous gel, backing layer 14, and a rate-controlling membrane or tie layer membrane would be sealed together about their periphery to prevent leakage. The adhesive layer 16 may optionally contain the drug. A strippable release liner (not shown) is normally provided along the exposed surface of adhesive layer 16 as removed prior to application of device 10 to the skin 18.

Alternatively, as shown in FIG. 2, transdermal therapeutic device 20 may be attached to the skin or mucosa of a patient by means of an adhesive overlay 22. Device 20 is comprised of a drug-containing reservoir 12. A backing layer 14 is provided adjacent one surface of reservoir 12. Adhesive overlay 22 maintains the device on the skin and may be fabricated with, or provided separately from, the remaining elements of the device. With certain formulations, adhesive overlay 22 may be preferable to the in-line contact adhesive 16 as shown in FIG. 1. This is true, for example, where the drug reservoir contains materials (such as, for example, an oily surfactant permeation enhancer), which adversely effects the adhesive properties of the in-line contact adhesive layer. Backing layer 22 is preferably slightly larger than reservoir 12, and, in this manner, prevents the materials in reservoir 12 from adversely interacting with the adhesive in overlay 22. Optionally, a rate-controlling membrane or tie layer membrane (not shown in FIG. 2) may be provided on the skin/mucosa side of reservoir 12. A strippable release liner 24 is provided with device 20 and is removed just prior to application of device 20 to the skin.

Alternatively, reservoir 24 may be in the form of a matrix containing the drug salt dispersed within a suitable adhesive, preferably a pressure sensitive adhesive. Such pressure sensitive adhesives include, but are not limited to, polysiloxanes, polyacrylates, polyurethanes, acrylic adhesives including cross linked or uncross linked acrylic copolymers, vinyl acetate adhesives, ethylene vinylacetate copolymers, and natural or synthetic rubbers including polybutadienes, polyisoprenes, and polyisobutylene adhesives, and mixtures and graft copolymers thereof. The matrix formulations according to this embodiment comprise the adhesive containing the drug salt laminated to a backing on one surface and to a release liner on the other. In addition to the drug salt, the matrix or carrier may also contain dyes, pigments, permeation enhancers, anti-irritants, inert fillers, excipients and other conventional components of pharmaceutical products or transdermal devices known to the art. For example, the matrix may also be provided with hydrophilic water absorbing polymers known in the art such as polyvinyl alcohol and polyvinyl pyrrolidone individually or in combination.

While the salt form of the normally irritating drug can be administered to human skin or mucosa by direct application to the skin or mucosa in the form of an ointment, gel, cream, or lotion, it is preferably administered through a skin patch or other known transdermal device such as described above which contains a saturated or unsaturated formulation of a salt form of the drug. The formulation may be aqueous or nonaqueous-based. Formulations should be designed to deliver the drug salt at the necessary flux rates.

Depending on the drug to be delivered, the drug carrier may be either aqueous or nonaqueous-based and is preferably an aqueous gel. If the drug has a low solubility in water, a non-aqueous solvent such as ethanol, propylene glycol, polyethylene glycol and the like is preferably added to aqueous formulations. Aqueous formulations typically comprise water and about 1–10 wt % of a hydrophilic polymer such as a gelling agent, such as hydroxyethylcellulose (HEC), hydroxypropylmethylcellulose (HPMC) or hydroxypropylcellulose (HPC). Typical non-aqueous gels are comprised of silicone fluid, natural or synthetic oils such as polybutene, or mineral oil. Mineral oil-based gels also typically contain 1–10 wt % of a gelling agent such as colloidal silicone dioxide. The suitability of a particular gel depends upon the compatibility of its constituents with either the drug salt, along with a permeation enhancer, if one is present, and any other components in the formulation.

When using an aqueous-based system, the reservoir matrix is preferably a hydrophilic polymer, eg, a hydrogel. When using a nonaqueous-based system, the reservoir matrix is preferably comprised of a hydrophobic polymer. Suitable polymeric matrices are well known in the transdermal delivery art, and, examples are listed in the above-mentioned patents previously incorporated herein by reference. A typical laminated system would consist essentially of a polymeric membrane and/or matrix such as ethylene vinyl acetate (EVA) copolymers, such as those described in U.S. Pat. No. 4,144,317, preferably having a vinyl acetate (VA) content in the range of from about 9% up to about 60% and more preferably about 9% to 40% VA. Polyisobutylene/oil polymers containing from 4–25% high molecular weight polyisobutylene and 20–81% low molecular weight polyisobutylene with the balance being an oil such as mineral oil or polybutene may also be used as the matrix material.

When a constant drug delivery rate is desired, the drug salt is present in the matrix or carrier at a concentration in excess of saturation, the amount of excess being a function of the desired length of the drug delivery period of the system. The drug salt may, however, be present at a level below saturation and without parting from this invention as long it is continuously administered to the same skin or mucosa site in an amount and for a period of time sufficient to be therapeutically effective.

In addition to the drug salt, which is essential to the invention, the matrix or carrier may also contain dyes, pigments, inert fillers, permeation enhancers, anti-irritants, excipients, and other conventional components of pharmaceutical products or transdermal devices known in the art as disclosed, for example, in the patents above. Additional permeation enhancers suitable for practice of this invention are disclosed in U.S. Pat. Nos. 4,568,343, 4,746,515, 4,764,379, 4,863,738, 4,865,848, 4,888,354, 4,900,555, 5,378,730, 5,629,019, 5,641,504, 5,686,097, and WO 95/09006, WO 95/01167, WO 96/37231, and WO 96/40259, for example, which are hereby incorporated in their entirety by reference.

The following examples are offered to illustrate the practice of the invention. It is important to note that this invention is not limited to any particular transdermal device or any other form of transdermal delivery, as are commonly known in the art. Nor is this invention limited to a particular formulation. Therefore, the embodiments described herein are merely illustrative and are not intended to limit the scope of the invention in any manner. All of the formulations used in the following Examples were provided at equal thermodynamic activity in order to provide normalized flux.

EXAMPLE 1

Chlorpromazine (pKa of 9.2) base and acetate formulations were assessed for their irritation potential after 24 hour application on the skin of hairless guinea pigs. Chlorpromazine base was formulated at 0.4% in a 3% HEC aqueous gel containing 70% (vol/vol) propylene glycol, and at 0.4%, 0.6%, and 0.8% in a 3% hydroxypropyl methyl cellulose (HPMC) K15M aqueous gel containing 20% (vol/vol) ethanol and 50% (vol/vol) propylene glycol. Chlorpromazine acetate was prepared extemporaneously by mixing equimolar amounts of chlorpromazine base and acetic acid. Chlorpromazine acetate was formulated at 0.5% and 1% (expressed as the base) in a 3% HEC aqueous gel. The formulations were brought to 100 mL by adding water. Each formulation contained approximately 0.36 $\mu$Ci $^3$H chlorpromazine per ml. and are identified in Table 1A below.

Hairless guinea pigs were washed with soapy water on both sides of the animal and wiped with acetone. 2 cm$^2$ systems were filled with 350 $\mu$L of the gel formulation. Two different systems were applied to each animal, one per side. Control gels consisted of water only, propylene glycol and water, and propylene glycol, water, and ethanol. Gel formulations were applied in quadruplicate. Animals were wrapped with Vetwrap® and placed into metabolic cages.

Guinea pigs were unwrapped at 24 hours and the systems were removed. Each site was washed twice with soapy water and cotton swab, rinsed twice with water and cotton swab, and dried with cotton swab. The swabs were placed in a scintillation vial along with the corresponding system. Skin sites were marked with indelible ink and the animals returned to their cages.

Scintillation vials were filled with 15 mL of extraction fluid and mixed for at least 48 hours. Standards (350 $\mu$L) were pipetted into systems and extracted in duplicate in the same manner.

Skin sites were measured with a Minolta chroma meter for redness 1 and 24 hour after removal of the systems. Duplicate aliquot samples (250 $\mu$L) of each extract were counted in a liquid scintillation counter to determine residual drug.

The difference between the initial and the residual drug content was calculated and divided by the time of application and the surface area in order to determine the flux.

The results were expressed as the difference between the redness of the skin in contact with the formulation (treated) and untreated skin (control) at the 1 hour time point. The chlorpromazine flux (expressed as the base), was evaluated by analyzing the residual drug from the systems. As seen in Table 1B, at equivalent flux, chlorpromazine acetate produced lower irritation as compared to that produced by chlorpromazine base.

TABLE 1B

FLUX AND REDNESS OF CHLORPROMAZINE GELS

| Formulation No. | Flux ($\mu$g/cm$^2$ · hr) | Redness |
| --- | --- | --- |
| 1 | 6.0 | 9.4 |
| 2 | 4.8 | 8.0 |
| 3 | 8.5 | 8.0 |
| 4 | 12.0 | 10.7 |
| 5 | 6.6 | 2.8 |
| 6 | 12.3 | 4.5 |

EXAMPLE 2

Fluoxetine (pKa=9.7) irritation and flux were studied in hairless guinea pigs. Formulations containing ethanol, propylene glycol, water, and fluoxetine base or fluoxetine acetate at various concentrations as shown in Table 2A were mixed together with $^3$H fluoxetine at a final concentration of 24 $\mu$Ci/mL fluoxetine. The formulations were brought to 100 mL by adding water and gelled with 4% HPMC.

TABLE 1A

CHLORPROMAZINE FORMULATIONS

| # | CHLORPROMAZINE BASE (vol/vol) | ACETIC ACID (vol/vol) | ETHANOL (vol/vol) | PROPYLENE GLYCOL (vol/vol) | HEC (wt/vol) | HPMC (wt/vol) |
| --- | --- | --- | --- | --- | --- | --- |
| 1 | 0.4 |  |  | 70 | 3 |  |
| 2 | 0.4 |  | 20 | 50 |  | 3 |
| 3 | 0.6 |  | 20 | 50 |  | 3 |
| 4 | 0.8 |  | 20 | 50 |  | 3 |
| 5 | 0.4 | 0.072 |  |  | 3 |  |
| 6 | 0.8 | 0.144 |  |  | 3 |  |

TABLE 2A

FLUOXETINE GEL FORMULATIONS

| # | FLUOXETINE BASE (wt/vol) | ACETIC ACID (vol/vol) | ETHANOL (vol/vol) | PROPYLENE GLYCOL (vol/vol) | HPMC (wt/vol) |
|---|---|---|---|---|---|
| 1 | 4.6 | | 30 | 45 | 4 |
| 2 | 3 | | 30 | 45 | 4 |
| 3 | 2.3 | | 30 | 45 | 4 |
| 4 | 2.2 | | 30 | 45 | 4 |
| 5 | 1.4 | | 30 | 45 | 4 |
| 6 | 1.2 | | 30 | 45 | 4 |
| 7 | 19.9 | 5.9 | 20 | 35 | 5 |
| 8 | 10.2 | 1.9 | 30 | 45 | 7 |
| 9 | 5.1 | 0.94 | 30 | 45 | 5 |
| 10 | 2.55 | 0.47 | 30 | 45 | 5 |

Skin sites on hairless guinea pigs were lightly washed. 2 cm² systems were filled with 350 µL of the gel formulation. One radioactive gel and one placebo gel (no drug) was applied to each guinea pig on opposite sides of the animal (n=3 per group) and an adhesive overlay was placed over each system. The guinea pigs were wrapped with Vetwrap® and returned to metabolic cages.

The systems were removed after 24 hours and the sites were thoroughly washed, dried, and marked with indelible ink for further evaluation. Photos and skin evaluations were taken at 2, 24, and 48 hours post-removal and were assessed according to the method of Draize et al. Urine was collected daily for 7 days and analyzed for radioactive content by scintillation counting. The fluoxetine flux was calculated from the urinary excretion data and was corrected by the percent urinary elimination following intracardiac administration of fluoxetine. Table 2B presents fluoxetine flux and PII values for the formulations tested.

The PII value is the averaged irritation of the three evaluation time points. As seen in Table 2B, at equivalent flux, fluoxetine acetate produced lower irritation as compared to that produced by fluoxetine base.

TABLE 2B

FLUOXETINE FLUX AND IRRITATION

| Formulation No. | Flux (µg/cm² · hr) | PII |
|---|---|---|
| 1 | 50.8 | 6.8 |
| 2 | 22.4 | 6 |
| 3 | 12.2 | 3.3 |
| 4 | 14.9 | 3.6 |
| 5 | 5.6 | 1.6 |
| 6 | 5.0 | 1.7 |
| 7 | 28.7 | 0.9 |
| 8 | 10.5 | 1.0 |
| 9 | 3.6 | 0.7 |
| 10 | 2.4 | 0.3 |

EXAMPLE 3

The effect of transdermal administration of fluoxetine acetate on the skin depot of drug accumulating in the skin was investigated. Fluoxetine systems were prepared by and were administered to hairless guinea pigs for 24 hours according to the procedure set forth in Example 2. Systems were removed at the end of day 1 and urinary excretion of fluoxetine was monitored for 5 days as described in Example 2. In other animals, fluoxetine was administered intravenously at time zero and urinary excretion was monitored for 4 days. FIG. 3 represents the urinary excretion of fluoxetine as a function of time. This graph shows that the kinetics of urinary excretion of fluoxetine is dramatically different according to the form administered transcutaneously. With fluoxetine base, skin depot is observed. With fluoxetine acetate (pH 6.5), the skin depot is reduced but is still present. With fluoxetine acetate acidified with excess acetic acid to pH 5, the skin depot is eliminated as the kinetics of elimination is close to that observed following intravenous administration of the drug.

EXAMPLE 4

The irritation and flux of various fluoxetine salts were studied in hairless guinea pigs according to the procedure set forth in Example 2. Formulations containing 20% (vol/vol) ethanol, 35% (vol/vol) propylene glycol and fluoxetine acetate, propionate, valerate, heptanoate, methane sulfonate, hydrochloride, hydrobromide, and nitrate at 0.65M were prepared by dissolving fluoxetine base in the ethanol propylene glycol mixture. Subsequently, the free acid was added in slight excess, followed by water to 100 ml and HPMC.

Figure 4:
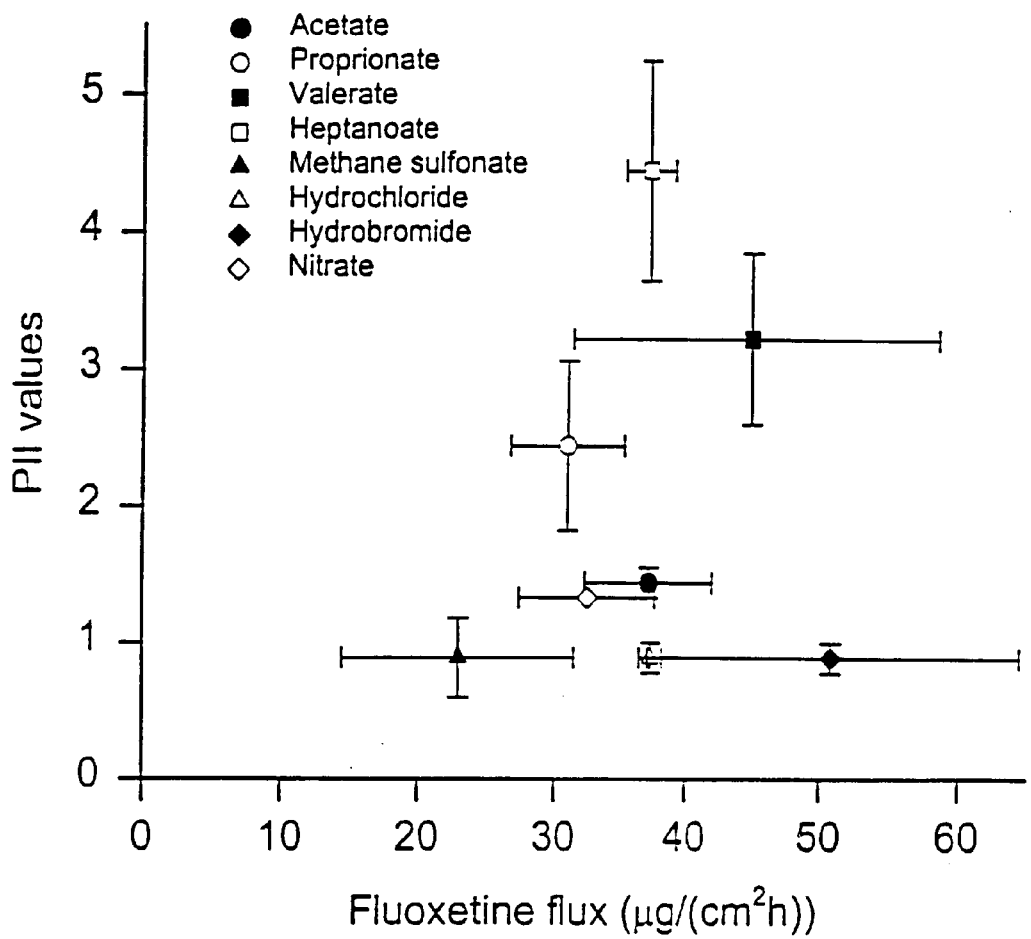
FIG. 4 is a graph depicting primary irritation scores (PII) vs. the transdermal flux of various salts of fluoxetine.
Figure 5:
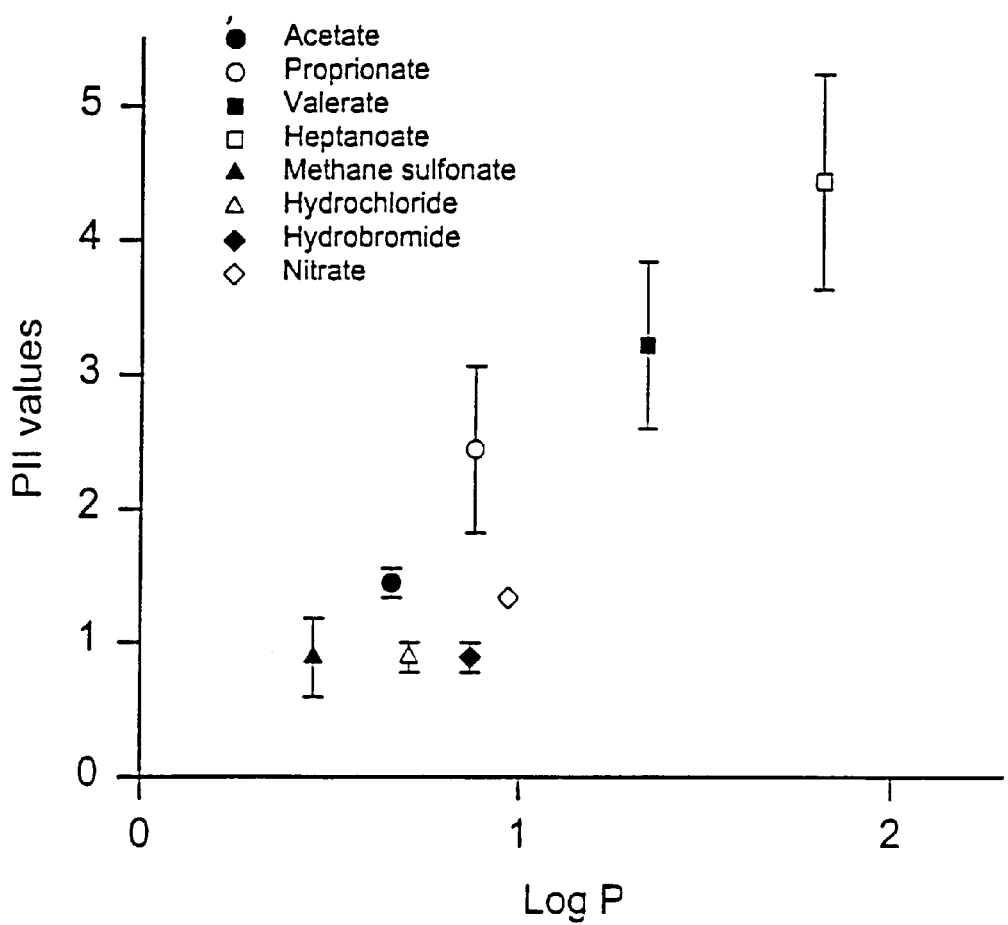
FIG. 5 is a graph depicting primary irritation scores (PII) vs. log P of various salts of fluoxetine.

In order to evaluate log P, the base form of fluoxetine was dissolved in octanol at 0.001 and 0.1 M and the salt form was prepared extemporaneously by equimolar addition of the free acid. 2.5 mL of this solution was added to 2.5 mL of water which contained 2.5 µCi of $^3$H fluoxetine. This mixture was gently mixed for 30 minutes and centrifuged. Aliquots (200 µL) of the octanol and the water phases were taken and analyzed for radioactive content as described in Example 2. From these data, fluoxetine concentrations in each phase were derived. Log P was calculated from the following formula: Log P=Log (fluoxetine concentration in octanol/fluoxetine concentration in water). Measurements of log P are given in Table 4. As seen in FIGS. 4 and 5, irritation of the different salts is mainly related to their partition coefficient between octanol and water (log P) and to a lesser extent to their flux.

TABLE 4

LOG P VALUES FOR FLUOXETINE SALTS

| Formulation | log P (0.001M) | log P (0.1M) |
|---|---|---|
| fluoxetine base | 1.51 | 2.21 |
| fluoxetine acetate | 0.05 | 0.66 |
| fluoxetine propionate | 0.20 | 0.88 |
| fluoxetine valerate | 0.71 | 1.34 |
| fluoxetine heptanoate | 1.27 | 1.81 |
| fluoxetine methane sulfonate | −0.29 | 0.45 |
| fluoxetine hydrochloride | −0.13 | 0.71 |
| fluoxetine hydrobromide | 0.05 | 0.87 |
| fluoxetine nitrate | 0.07 | 0.97 |

EXAMPLE 5

An in vivo study was performed using hairless guinea pigs and the urinary excretion model set forth in Example 2 to study the effect of various oxybutynin (pKa=9.9) salts on flux and skin irritation. All gels contained 0.6M oxybutynin, 20% ethanol, 35% propylene glycol, water, acid and 4–8% hydroxypropylmethyl cellulose (depending on water content). The acids used were acetic, propionic, valeric, heptanoic, methane sulfonic, hydrochloric, hydrobromic, and nitric. Formulations were prepared by dissolving oxybutynin base in the ethanol propylene glycol mixture. Subsequently, the free acid was added in slight excess, followed by water and HPMC. Excess acid was added to the gels in order to bring the pH to 5. All oxybutynin gels contained approximately 14 μCi $^{14}$C oxybutynin per ml. Log P values were measured according to the procedure set forth in Example 4 and are set forth below in Table 5.

TABLE 5

LOG P VALUES FOR OXYBUTYNIN SALTS

| Formulation | log P (0.001M) | log P (0.1M) |
|---|---|---|
| oxybutynin base | 1.09 | 1.30 |
| oxybutynin acetate | 0.57 | 0.54 |
| oxybutynin propionate | 0.69 | 0.72 |
| oxybutynin valerate | 0.90 | 1.00 |
| oxybutynin heptanoate | 1.05 | 1.19 |
| oxybutynin methane sulfonate | −0.46 | 0.29 |
| oxybutynin hydrochloride | −0.13 | 0.33 |
| oxybutynin hydrobromide | −0.13 | 0.66 |
| oxybutynin nitrate | −0.10 | 0.70 |

The skin of 24 hairless guinea pigs was lightly washed, rinsed, and dried. Passive systems contained a 2 cm$^2$ reservoir capable of holding 350 μl of gel. Each guinea pig received two systems, one containing radioactive oxybutynin gel and one containing appropriate placebo gel, which were placed on opposite sides of the animal. Each oxybutynin gel was tested in triplicate. Systems were held in place with a secondary overlay and then wrapped lightly with Vetwrap®. The animals were then placed into metabolic cages with free access to food and water.

24 hours after application, the systems were removed. The radioactive sites were thoroughly washed, rinsed, and dried. Application sites were marked with indelible ink for further evaluation. Guinea pigs were returned to their cages for another 3 days for a total of 4 days.

Figure 6:
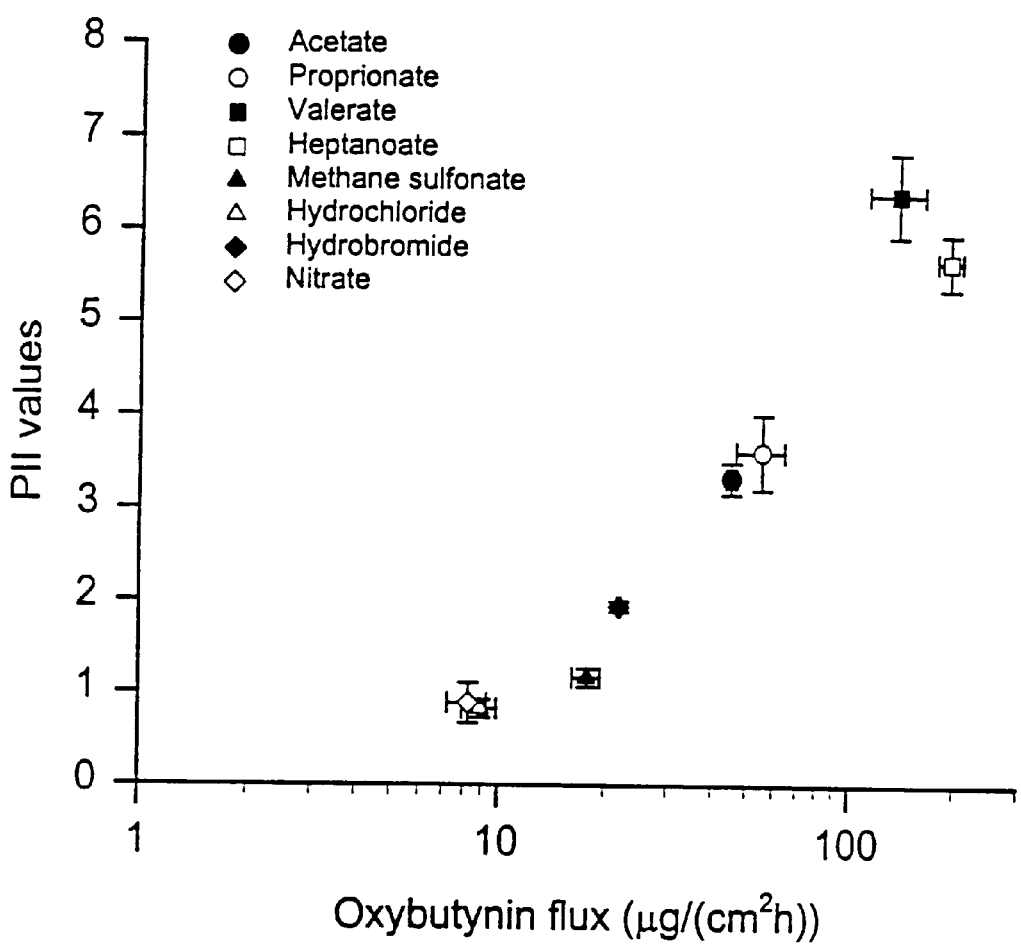
FIG. 6 is a graph depicting primary irritation scores (PII) vs. the transdermal flux of various salts of oxybutynin.
Figure 7:
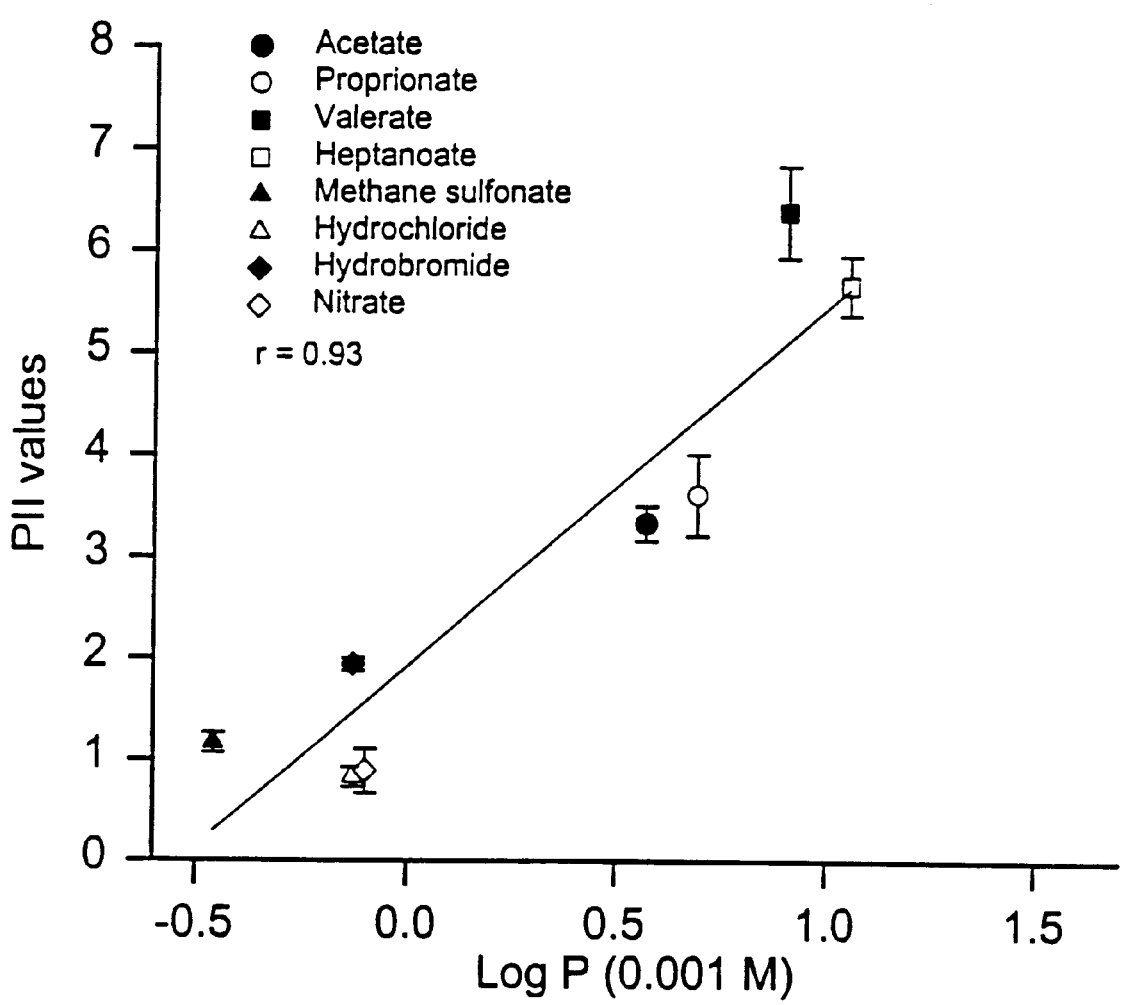
FIG. 7 is a graph depicting primary irritation scores (PII) vs. log P of various salts of oxybutynin.

Skin sites were evaluated 1, 24, and 48 hours post-removal using the primary skin irritation scoring system of Draize et al. Urine was collected daily. One ml samples of urine from each daily collection was counted for radioactivity content which was used to determine flux of oxybutynin as set forth in Example 2. The results are depicted in FIGS. 6 and 7. These results show that oxybutynin salts with log P (0.001 M) values between −0.5 and 1 flux at a therapeutically effective rate with minimum irritation.

EXAMPLE 6

The study performed in Example 2 was repeated using paroxetine (pKa=9.8) as the drug. All paroxetine gels contained paroxetine base, 40% ethanol, 35% propylene glycol, water, and 5% HPMC. Placebo gels were identical with water replacing the paroxetine. Paroxetine acetate gels contained paroxetine base, acetic acid, water, and 2% HEC. The placebos were identical except did not contain any paroxetine and the pH was adjusted to 5 with sodium hydroxide. All paroxetine gels contained approximately 28 μCi $^3$H paroxetine per ml.

Figure 8:
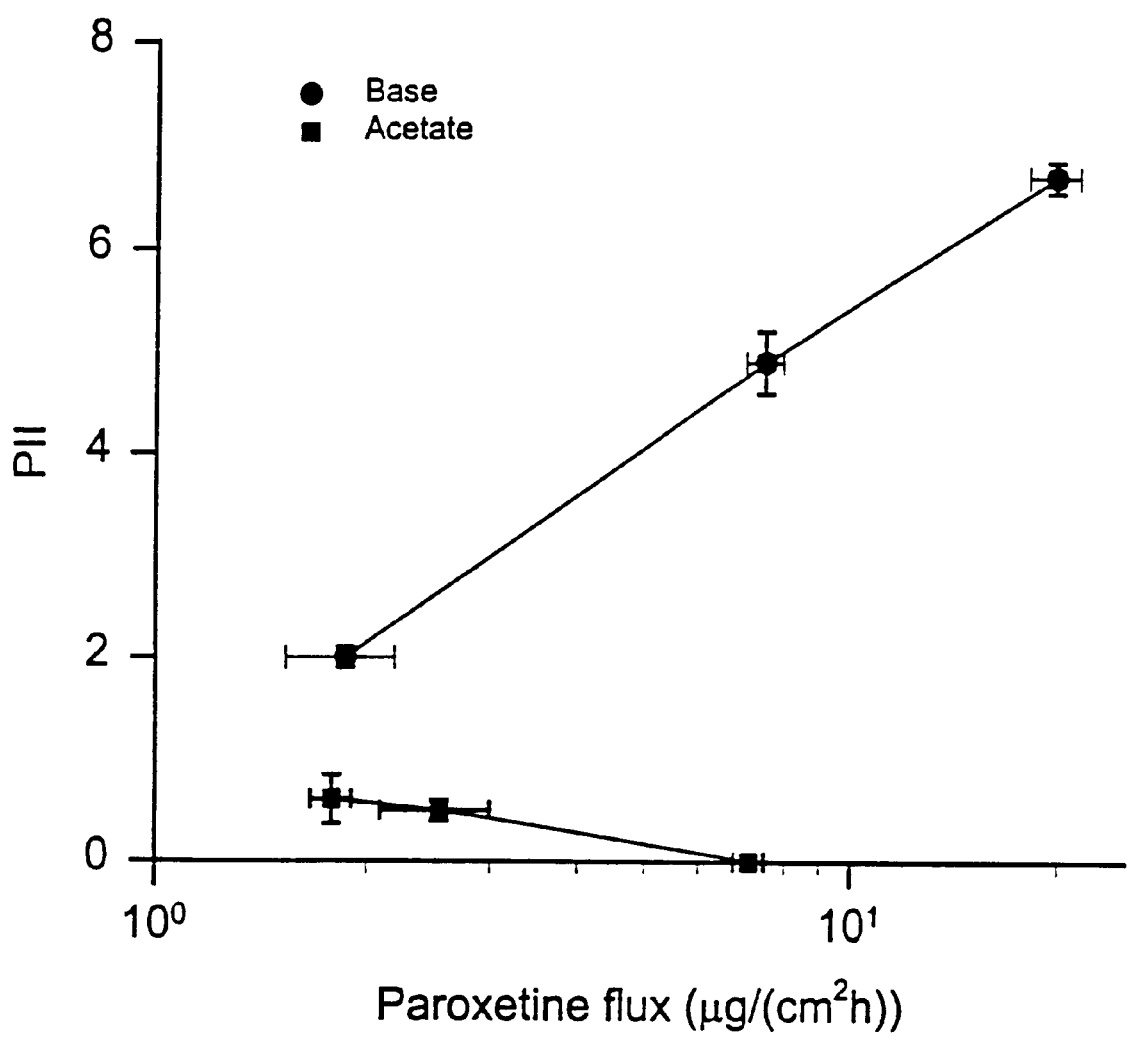
FIG. 8 is a graph depicting primary irritation scores (PII) vs. the transdermal flux of paroxetine.

Irritation of the paroxetine acetate gels was reduced as compared to the paroxetine base gels at equivalent flux as shown in FIG. 8.

EXAMPLE 7

Drug/permeation enhancer reservoirs were prepared by mixing ethylene vinyl acetate having a vinyl acetate content of 40 percent ("EVA 40", USI Chemicals, Illinois), with fluoxetine acetate, hydrocortisone base (HC), glycerol monolaurate, and a cosolvent comprising lauryl lactate (LL), dodecyl acetate (DA), or methyl laurate (ML) in a "Brabender" type mixer as set forth in Table 7. After blending, the mixture was calendered into a 6 mil. thick film. The film was then laminated to a 1 mil. unsiliconized polyethylene backing on one side. The composition of the drug reservoirs is shown in Table 7.

TABLE 7

Drug/Permeation Enhancer Reservoir Composition (weight percent)

| Sample # | Formulation | Weight Percent |
|---|---|---|
| 1 | fluoxetine acetate/EVA/HC/GML/ML | 33/47/5/10/5 |
| 2 | fluoxetine acetate/EVA/HC/GML/DA | 33/47/5/10/5 |
| 3 | fluoxetine acetate/EVA/HC/GML/LL | 33/47/5/10/5 |
| 4 | fluoxetine acetate/EVA/HC | 33/62/5 |
| 5 (control) | fluoxetine base/EVA | 33/67 |

Circular pieces of human epidermis were placed with stratum corneum facing up. The release liner of the laminate was removed and the fluoxetine releasing side of the system was centered over the stratum corneum side of the epidermis which had been blotted dry just prior to use. The edges of epidermis were then folded around the system so that none of the system edge was exposed to the receptor solution. This assembly was then mounted on a Teflon® holder of a release rate rod using nylon mesh and metal string. A known volume of receptor solution (0.001 M $H_3PO_4$) was then placed in a test tube and was equilibrated at 35° C. The test tube was placed in a water bath and maintained at 35° C. The Teflon rod with system and epidermis attached was then reciprocated within the test tube by attaching the rod to a motor which caused constant vertical mixing.

Figure 9:
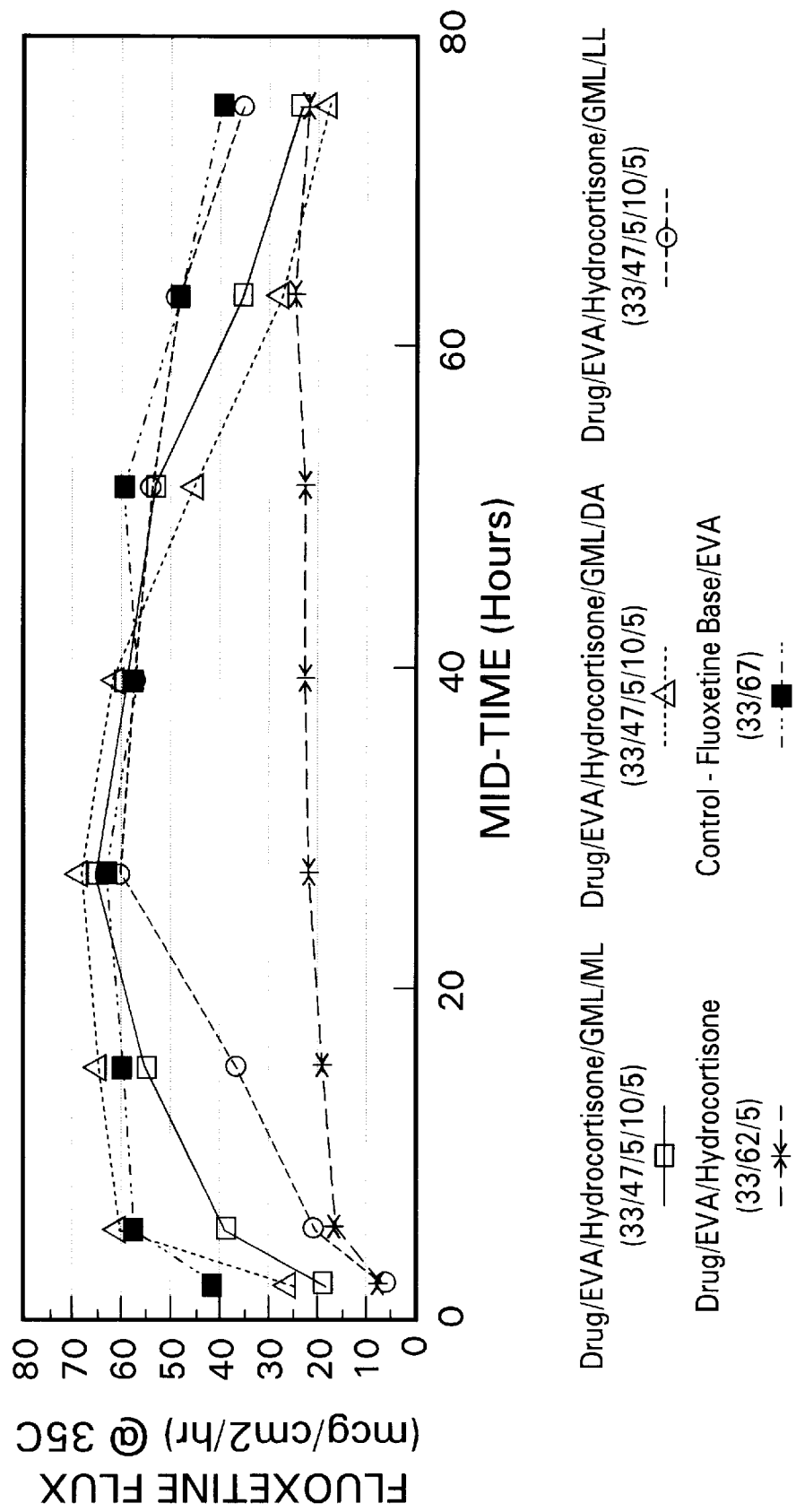
FIG. 9 is a graph depicting the flux of fluoxetine acetate through epidermis from EVA systems with various permeation enhancers.
Figure 10:
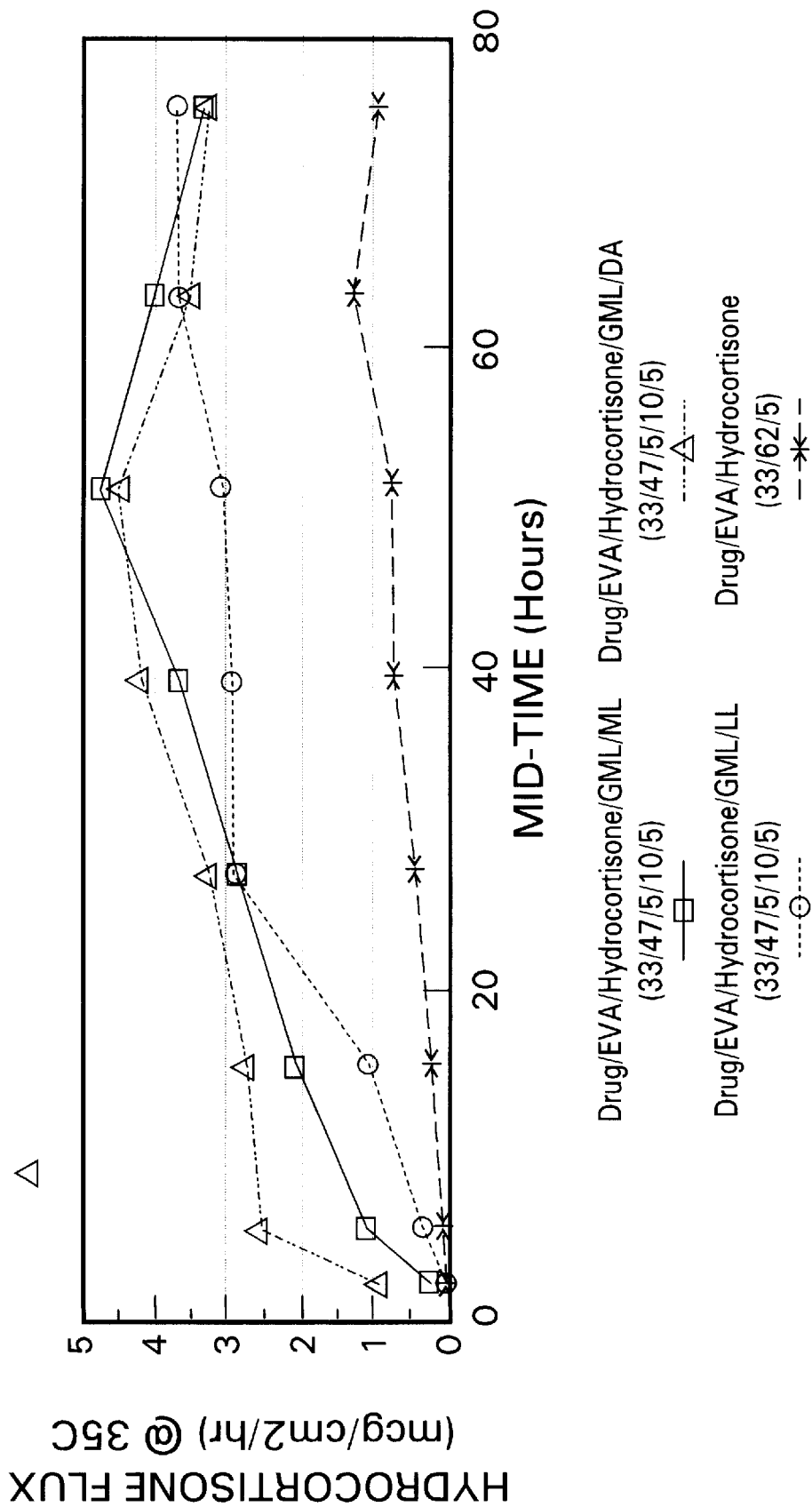
FIG. 10 is a graph depicting the flux of hydrocortisone through epidermis from EVA systems containing fluoxetine acetate with various permeation enhancers.

At given time intervals, the entire receptor solution was removed from the test tubes and replaced with an equal volume of fresh receptor solutions previously equilibrated at 35° C. The receptor solutions are stored in capped vials at 4° C. until assayed for fluoxetine content by HPLC. From the drug concentration and the volume of the receptor solutions, the area of permeation and the time interval, the flux of the drug through the epidermis was calculated as follows: (drug concentration X volume of receptor)/(area×time)=flux (μg/cm$^2$ hr). The in vitro flux of fluoxetine acetate through epidermis at 35° C. is shown in FIG. 9. The in vitro flux of hydrocortisone through epidermis at 35° C. is shown in FIG. 10.

EXAMPLE 8

Drug reservoirs containing fluoxetine acetate, fluoxetine hydrochloride, or fluoxetine maleate were prepared according to the procedure set forth in Example 7. An adhesive layer was laminated to some of the drug reservoir laminates. The laminate formulations are set forth in Table 8A. The acrylate adhesive used was a 2 mil layer of Acrylate #73–9259 (National Starch, Bridgewater, N.J.). The PIB was a mixture of 90 wt % low molecular weight PIB (MW 35,000) and 10 wt % high molecular weight PIB (MW 1,200,000) with a 1 mil thickness.

TABLE 8A

Drug/Permeation Enhancer Reservoir Composition (weight percent)

| Sample # | Formulation | Adhesive | Weight Percent |
|---|---|---|---|
| 1 | fluoxetine acetate/EVA/HC | acrylate | 33/62/5 |
| 2 | fluoxetine acetate/EVA | acrylate | 33/67 |

TABLE 8A-continued

Drug/Permeation Enhancer Reservoir Composition (weight percent)

| Sample # | Formulation | Adhesive | Weight Percent |
|---|---|---|---|
| 3 | fluoxetine acetate/EVA/HC | PIB | 33/62/5 |
| 4 | fluoxetine acetate/EVA | PIB | 33/67 |
| 5 | fluoxetine hydrochloride/ EVA/GML/DA/HC | acrylate | 33/47/10/5/5 |
| 6 | fluoxetine hydrochloride/ EVA/GML/DA | acrylate | 33/52/10/5 |
| 7 | fluoxetine maleate/ EVA/GML/DA/HC | none | 33/47/10/5/5 |
| 8 | fluoxetine maleate/EVA/GML/DA | none | 33/52/10/5 |

Skin fluxes were obtained using the procedure set forth in Example 7. Average skin fluxes (average of 2 skins) over a 72 hour period are given in Table 8B. Additionally, skin irritation was measured in a three day wear study conducted of hairless guinea pigs. Irritation was observed at ½ hour, 24 hours, and 48 hours after removal of the systems. Primary irritation index (PII) scores were determined using the Draize et al. method and are given in Table 8B.

TABLE 8B

Average Skin Flux and Primary Irritation Index Scores

| Sample | Average Flux ($\mu$g/cm² · hr) | PII Score |
|---|---|---|
| 1 | 12 | 1.4 |
| 2 | 13 | 3.1 |
| 3 | 10 | 4.4 |
| 4 | 18 | 5.9 |
| 5 | 8 | 4.3 |
| 6 | 9 | 4.5 |
| 7 | 19 | 1.6 |
| 8 | 17 | 2.4 |

EXAMPLE 9

An in vitro study was performed using hairless guinea pigs and the urinary excretion model to study the effect of pH of fluoxetine acetate gels on flux and skin irritation. All fluoxetine acetate gels contained 0.66M fluoxetine, water, acetic acid, and 3% hydroxyethyl cellulose. Placebo gels were made at the corresponding pH and contained water, acetic acid, 3% HEC and sodium hydroxide (1 N) to adjust pH. All fluoxetine gels contained approximately 21 $\mu$Ci ³H fluoxetine per ml. The gel formulations and their respective pH are shown below in Table 9.

TABLE 9

FLUOXETINE FORMULATIONS

| # | FLUOXETINE BASE (wt/vol) | ACETIC ACID (vol/vol) | NaOH (vol/vol) | HEC wt/vol | pH |
|---|---|---|---|---|---|
| 1 | 20.5 | 3.8 | | 3 | 6.74 |
| placebo | | 3.8 | 6.6 | 3 | 6.62 |
| 2 | 20.5 | 4.4 | | 3 | 5.34 |
| placebo | | 4.4 | 6.6 | 3 | 5.3 |
| 3 | 20.5 | 5 | | 3 | 5.01 |
| placebo | | 5 | 6.6 | 3 | 5.07 |
| 4 | 20.5 | 5.9 | | 3 | 4.82 |
| placebo | | 5.9 | 6.6 | 3 | 4.8 |
| 5 | 20.5 | 7.5 | | 3 | 4.63 |
| placebo | | 7.5 | 6.6 | 3 | 4.53 |
| 6 | 20.5 | 10.5 | | 3 | 4.48 |
| placebo | | 10.5 | 6.6 | 3 | 4.37 |
| 7 | 20.5 | 15.7 | | 3 | 4.18 |
| placebo | | 15.7 | 6.6 | 3 | 4.08 |
| 8 | 20.5 | 25 | | 3 | 3.87 |
| placebo | | 25 | 6.6 | 3 | 3.7 |

Figure 11:
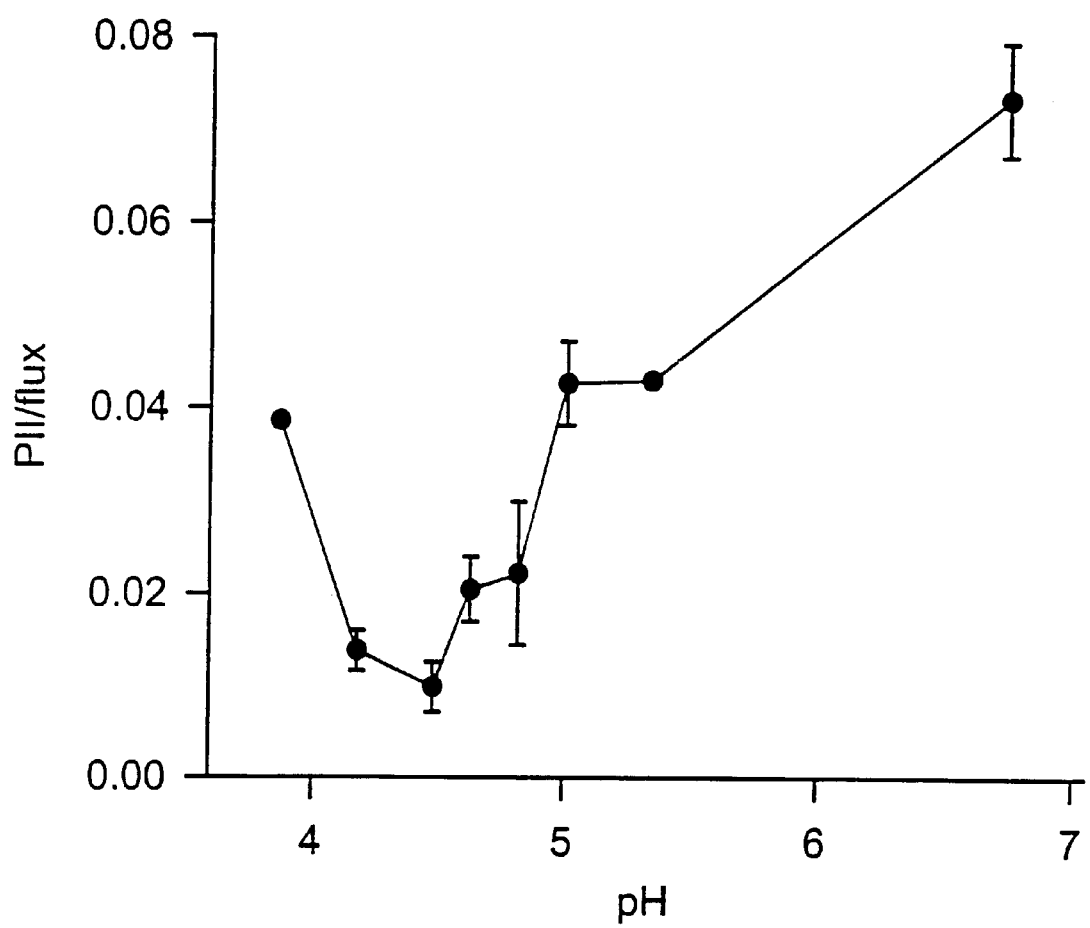
FIG. 11 is a graph depicting the effect of pH on fluoxetine induced skin irritation.

Fluoxetine flux and skin irritation were assessed using the procedure set forth in Example 5. The results are in the plot of PII/flux as a function of pH as depicted in FIG. 11. FIG. 11 shows an optimal pH range of 4–5 and/or an optimal range of free acetic acid concentration of about 1–15% at which irritation is greatly reduced while flux is not compromised.

While the invention has been described with reference to specific embodiments, it will be apparent to those skilled in the art that many alternatives, modifications, and variations may be made. Accordingly, it is intended to embrace all such alternatives, modifications, and variations that may fall within the spirit and scope of the appended claims.

What is claimed is:

1. A device for administering through the skin a therapeutically effective amount of an irritating, non-zwitterionic drug over an administration period, said device comprising:
   a) a reservoir comprising a salt of said drug having surface activity and a value of log P lower than about 1.0; said reservoir further characterized by being free of a separate irritation reducing agent;
   b) a backing adjacent the skin distal surface of the reservoir; and
   wherein the drug is administered at a clinically acceptable irritation level when maintained in skin contact over said administration period.

2. A device according to claim 1 wherein the drug is a basic drug comprising at least one pKa between about 6.0–12.0.

3. A device according to claim 2, wherein the reservoir contains a conjugated or non-conjugated weak acid in order to control pH within 3–6 pH units below the pKa of the drug.

4. A device according to claim 3 wherein the weak acid is selected from the group consisting of acetic acid, propionic acid, lactic acid, malic acid, citric acid, succinic acid, maleic acid, gluconic acid, glucuronic acid, 3-hydroxyisobutyrate, 2-hydroxyisobutyrate, pyruvic acid, tartaric acid, tartronic acid, fumaric acid, and glycolic acid.

5. A device according to claim 2 wherein the salt is selected from the group consisting of acetate, chloride, bromide, citrate, succinate, maleate, glycolate gluconate, glucuronate, 3-hydroxyisobutyrate, 2-hydroxyisobutyrate, lactate, malate, pyruvate, tartarate, tartronate, mesylate, nitrate, benzene sulfonate, sulfate, sulfonate, and fumarate.

6. A device according to claim 1 wherein the drug is an acidic drug comprising at least one pKa between about 2.0–8.0.

7. A device according to claim 6 wherein the reservoir contains a conjugated or non-conjugated weak base in order to control pH within 3–6 pH units above the pKa of the drug.

8. A device according to claim 7 wherein the weak base is selected from the group consisting of ammonium, monoethanolamine, diethanolamine, triethanolamine, tromethamine, lysine, methylglucamine, morpholine, histidine, and arginine.

9. A device according to claim 6 wherein the salt is selected from the group consisting of sodium, potassium, calcium, magnesium, ammonium, monoethanolamine, diethanolamine, triethanolamine, tromethamine, lysine, methylglucamine, morpholine, histidine, and arginine.

10. A device according to claim 3 or 7 wherein the mole ratio of weak acid or base/drug is about 1–7.

11. A device according to claim 10 wherein the mole ratio is about 1.5–5.5.

12. A device according to claim 3 wherein the pH is maintained at least 4 pH units below the pKa of the drug.

13. A device according to claim 7 wherein the pH is maintained at least 4 pH units above the pKa of the drug.

14. A device according to claim 1 wherein the drug salt has a log P value of less than 0.8.

15. A device according to claim 1 wherein the drug is selected from amphiphillic drugs having a molecular weight of less than 1000.

16. A device according to claim 1, wherein the drug salt comprises a critical micelle concentration of less than 0.5 M.

17. A device according to claim 16, wherein the critical micelle concentration is about $10^{-6}$–$10^{-1}$ M.

18. A device according to claim 1, wherein the drug is selected from the group consisting of fluoxetine, paroxetine, citalopram, olanzapine, raloxifen, fentanyl, chlorpromazine, and oxybutynin.

19. A device according to claim 1, wherein the drug salt is fluoxetine acetate.

20. A device according to claim 1 wherein the reservoir comprises an aqueous gel.

21. A device according to claim 1, wherein the reservoir contains a non-aqueous solvent.

22. A device according to claim 21, wherein the solvent is selected from the group consisting of ethanol, propylene glycol, and polyethylene glycol.

23. A device according to claim 1, wherein the reservoir comprises a polymeric matrix.

24. A device according to claim 23, wherein the polymeric matrix is selected from the group consisting of ethylene vinyl acetate copolymers, polyacrylates, polysiloxanes, polyurethanes, and polyisobutylenes.

25. A device according to claim 1 further comprising a permeation enhancing amount of a permeation enhancer.

26. A method for reducing skin or mucosal irritation during administration through the skin of a therapeutically effective amount of an irritating, non-zwitterionic drug over an administration period comprising:
   a) providing a carrier with an amount of a salt of said drug, said drug salt having surface activity and a value of log P lower than about 1.0; said reservoir further characterized by being free of a separate irritation reducing agent and
   b) placing said carrier in drug transmitting relation with the skin or mucosa of an individual, where in the drug is administered at a clinically acceptable irritation level when maintained in skin contact over said administration period.

27. A method for reducing the skin depot of drug accumulated in the skin during administration through the skin a therapeutically effective amount of an irritating non-zwitterionic drug over an administration period comprising the steps of:
   a) providing a carrier with an amount of a salt of said drug, said drug salt having surface activity and a value of log P lower than about 1.0; and
   b) placing said carrier in drug transmitting relation with the skin or mucosa of an individual, where in the drug is administered at a clinically acceptable irritation level when maintained in skin contact over said administration period.

* * * * *

UNITED STATES PATENT AND TRADEMARK OFFICE
CERTIFICATE OF CORRECTION

PATENT NO. : 6,203,817 B1
DATED : March 20, 2001
INVENTOR(S) : Cormier, et al.

It is certified that error appears in the above-identified patent and that said Letters Patent is hereby corrected as shown below:

Column 20,
Line 24, insert -- of -- between "skin" and "a";
Line 32, "where in" should be -- wherein --.

Signed and Sealed this

Sixth Day of November, 2001

Attest:

NICHOLAS P. GODICI
Attesting Officer
Acting Director of the United States Patent and Trademark Office